(12) United States Patent
Furuta

(10) Patent No.: US 7,211,681 B2
(45) Date of Patent: May 1, 2007

(54) ESTER PRODUCTION METHOD BY TRANSESTERIFICATION REACTION USING SOLID ACID CATALYST

(75) Inventor: Satoshi Furuta, Toda (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 10/544,822

(22) PCT Filed: Mar. 19, 2004

(86) PCT No.: PCT/JP2004/003731

§ 371 (c)(1),
(2), (4) Date: Aug. 5, 2005

(87) PCT Pub. No.: WO2004/085584

PCT Pub. Date: Oct. 7, 2004

(65) Prior Publication Data

US 2006/0149087 A1    Jul. 6, 2006

(30) Foreign Application Priority Data

Mar. 26, 2003    (JP) .............................. 2003-083979
Dec. 1, 2003    (WO) ....................... PCT/JP03/15323

(51) Int. Cl.
     *C07C 51/43*    (2006.01)
     *C07C 67/02*    (2006.01)

(52) U.S. Cl. ....................................... 554/174; 560/234

(58) Field of Classification Search ................ 554/174; 560/234
See application file for complete search history.

(56) References Cited

U.S. PATENT DOCUMENTS 6,204,424 B1    3/2001    Yadav 6,376,701 B1 *    4/2002    Chavan et al. .............. 560/174

FOREIGN PATENT DOCUMENTS

| JP | 6-313188 | 11/1994 |
|---|---|---|
| JP | 7-197047 | 8/1995 |
| JP | 9-235573 | 9/1997 |
| JP | 2000-143586 | 5/2000 |
| WO | WO 01/88072 A1 | 11/2001 |

OTHER PUBLICATIONS

Transesterification of Sunflower Oil in Situ, Siler-Marinkovic, et al., Fuel, IPC Science and Technology Press, 1998, pp. 1389-1391.

Measurement of Heat of Argon Adsorption for the Evaluation of Relative Acid Strength of Some Sulfated Metal Oxides and H-type Zeolites, Matsuhashi, et al., Journal of Physical Chemistry B, vol. 105, No. 40, pp. 9669-9671 (2001).

* cited by examiner

*Primary Examiner*—J. Parsa
(74) *Attorney, Agent, or Firm*—Flynn, Thiel, Boutell & Tanis, P.C.

(57) ABSTRACT

It is an object of this invention to provide a method for producing an ester by a transesterification reaction in which the reaction can be stably performed in a short time at a pressure approximately equal to normal pressure. The ester is produced by a transesterification reaction in which a starting material ester and an alcohol are brought into contact with a solid acid catalyst that displays the characteristics of a very strong acid in terms of the absolute value of argon adsorption heat ranging from 15 to 22 kJ/mol. In particular, it is preferable that the starting material ester in a liquid phase and alcohol in a vapor phase be brought into contact with the solid acid catalyst, and that the starting material ester be oil or fat, and the alcohol be methanol or ethanol.

6 Claims, No Drawings

ESTER PRODUCTION METHOD BY TRANSESTERIFICATION REACTION USING SOLID ACID CATALYST

TECHNICAL FIELD

The present invention relates to a method for producing a fatty acid ester or other ester by a transesterification reaction from a triglyceride, diglyceride, monoglyceride, or another starting material ester.

BACKGROUND ART

As disclosed, for example, in the following patent documents, transesterification reactions are used to produce fatty acid esters, with oils and fats, which are esters of fatty acids and glycerol, serving as starting materials. Caustic soda and other alkali catalysts, as well as zinc catalysts, lipases, and the like are used as the catalysts. It has also been proposed to perform reactions in a supercritical state without adding a catalyst.

Patent document 1 Patent Publication No. 9-235573A
Patent document 2 Patent Publication No. 7-197047A
Patent document 3 Patent Publication No. 2000-143586A

DISCLOSURE OF THE INVENTION

The above reactions are time-consuming, and the process for separating the catalyst following the reaction is needed when caustic soda or another alkali catalyst is used. In addition, when the starting material contains a large amount of free fatty acids, a pretreatment must be performed in order to remove these acids. Alternatively, saponification reactions may inhibit the transesterification reaction and bring about other drawbacks. The reaction must commonly be performed at a high pressure when a zinc catalyst is used or when the reaction is conducted in a supercritical state.

It is an object of the present invention to provide a method for producing an ester by a transesterification reaction in which the reaction can be performed in a short time at a pressure approximately equal to normal pressure.

The inventors discovered that bringing the starting material ester and alcohol into contact with a solid acid catalyst that displays the characteristics of a very strong acid within a specific range could stably advance a transesterification reaction. It is preferable in this case to bring a liquid-phase starting material ester and a vapor-phase alcohol into contact with the solid acid catalyst.

BEST MODE FOR CARRYING OUT THE INVENTION

Starting Material Ester

The starting material ester used in the present invention may be any ester containing an ester compound as its principal component, and may be a polyester. In particular, a glyceride of a saturated or unsaturated aliphatic carboxylic acid (carbon number of the carboxylic acid: about 8 to 24) is preferably used. Specifically, triglycerides referred to as oils and fats are preferably used. Examples of such oils and fats include soybean oil, coconut oil, olive oil, peanut oil, cottonseed oil, sesame oil, palm oil, castor oil, and other vegetable oils and fats, as well as beef tallow, lard, horse fat, whale oil, sardine oil, mackerel oil, and other animal oils and fats. The content of free fatty acids in the starting material ester is 0 wt % to 30 wt %, and preferably 1 wt % to 20 wt %.

Alcohol

The alcohol used in the present invention is an alcohol with a carbon number of 1 to 3, and preferably methanol or ethanol, but a polyhydric alcohol may also be used. A mixture of these may also be used.

Solid Acid Catalyst

A solid acid catalyst which exhibits a very strong acidity in terms of the absolute value of argon adsorption heat ranging from 15 to 22 kJ/mol, preferably 15 to 20 kJ/mol, is used in the present invention. When the acidity is expressed in terms of Hammett acidity function Ho, it is preferably within the range of −12 to −15. The argon adsorption heat is the absolute value of adsorption heat obtained by heating the measurement object to 300° C. while evacuating, introducing argon at the temperature of liquid nitrogen, and measuring the amount of adsorption by volumetry. The details are disclosed in *J. Phys. Chem. B*, Vol. 105, No. 40, p. 9667-(2001). The adsorption heat is commonly 50 kJ/mol or less.

It is preferable to use a solid acid catalyst in which a sulfuric group or a Group VI metal component is supported on the surface of a crystalline metal oxide. The metal oxide may be an oxide of a single metal or a combination of metals selected from zirconium, hafnium, titanium, silicon, germanium, tin, and the like. Specific examples of such catalysts include sulfated zirconia-based catalysts, sulfated tin oxide-based catalysts and other catalysts, which are described below. Group IV metal/Group VI metal-based catalysts (especially, tungsten/zirconia-based catalysts) are particularly preferable.

The specific surface area of the catalyst is preferably 50 to 500 $m^2/g$, particularly 60 to 300 $m^2/g$, and more particularly 70 to 200 $m^2/g$. The specific surface area can be measured by the commonly known BET method. The pore structure of the catalyst can be measured by a nitrogen adsorption for pore diameters in the range of 0.002 to 0.05 μm, and by a mercury porosimetry for pore diameters in the range of 0.05 to 10 μm. The pore volume with a pore diameter of 0.002 to 10 μm is preferably at least 0.2 $cm^3/g$, with a pore volume of 0.25 $cm^3/g$ to 1.0 $cm^3/g$ being particularly preferable. The central pore diameter of pore diameters in the range of 0.002 to 0.05 μm is preferably 50 to 200 Å, and particularly preferably 70 to 150 Å.

The catalyst preferably has a shaped form, or a so-called pellet shape, rather than a powdered shape, and one with a size of 0.5 to 20 mm can be readily obtained. A catalyst whose mean grain size is 0.5 to 20 mm, and particularly 0.6 to 5 mm, is preferably used. The mechanical strength of the catalyst, expressed as the side crushing strength of a cylindrical pellet with a diameter of 1.5 mm, is 1.0 kg or greater, and preferably 2.0 kg or greater.

Sulfated Zirconia-Based Catalyst

In the sulfated zirconia-based catalyst, the metal component of at least part of the metal oxide comprises a zirconia (zirconium oxide) portion, which is a zirconium compound, and contains a sulfureous component. Generally, it is known that this type of catalyst has a Hammett acidity function Ho of −16.1. "Metal oxide" is defined as one comprising a hydrated metal oxide. The catalyst preferably comprises zirconia in an amount of 20 to 72 wt %, and particularly 30 to 60 wt %, in terms of the weight of the zirconium element. The proportion of the sulfureous component is 0.7 to 7 wt %, preferably 1 to 6 wt %, and particularly 2 to 5 wt %, in terms of the weight of the sulfur element. Catalytic activity decreases if the proportion of the sulfureous component is too high or too low.

The zirconia portion preferably substantially comprises tetragonal zirconia. This can be confirmed by powder X-ray analysis or, in more specific terms, by the diffraction peak of tetragonal ammonia at 2θ=30.2° with the CuKα line. It is preferable that crystallization proceed to an extent that can be confirmed by means of a diffraction peak, and that no monoclinic zirconia be present. The ratio S28/S30 is preferably 1.0 or less, and particularly 0.05 or less, where S30 is the area of the diffraction peak of tetragonal zirconia with 2θ=30.2°, and S28 is the area of the diffraction peak of monoclinic zirconia with 2θ=28.2°.

In addition, the catalyst preferably comprises aluminum oxide in an amount of 5 to 30 wt %, and particularly 8 to 25 wt %, in terms of the weight of the aluminum element. This alumina portion is preferably crystallized, and, in particular, substantially consists of γ-alumina.

Sulfated Tin Oxide-Based Catalyst

The sulfated tin oxide-based catalyst comprises a tin oxide portion, in which tin is the metal component of at least part of the metal oxide, and also contains a sulfureous component. Generally, it is known that this type of catalyst has a Hammett acidity function Ho of −18.0. "Metal oxide" is defined as one comprising a hydrated metal oxide. The catalyst preferably comprises tin oxide in an amount of 20 to 72 wt %, and particularly 30 to 72 wt %, in terms of the weight of the tin element. The proportion of the sulfureous component is 0.7 to 10 wt %, preferably 1 to 9 wt %, and particularly 2 to 8 wt %, in terms of the weight of the sulfur element. Catalytic activity decreases if the proportion of the sulfureous component is too high or too low. The specific surface area of the catalyst is preferably 100 m²/g or greater, and particularly 100 to 200 m²/g.

As a characteristic of the tin oxide, amorphous tin oxide may also be used, but one consisting essentially of an oxide having a tetragonal crystal structure is preferred. This can be confirmed by powder X-ray analysis or, in more specific terms, by the diffraction peak at 2θ=26.6° with the CuKα line. Crystallization preferably proceeds to an extent that can be confirmed by means of a diffraction peak, and the crystallite diameter is preferably 10 to 50 nm, and more preferably 20 to 45 nm.

The method for producing the sulfated tin oxide-based catalyst is not particularly limited and, as an example, it is possible to use a production method in which a sulfur-containing compound is added to tin oxide, and the product is then calcined. The sulfated tin oxide-based catalyst may be in the form of a powder or a molded article, or in the form of a catalyst in which tin oxide is supported on the surface of a support consisting of components other than tin oxide.

The tin oxide may be used in any form, and metastannic acid is used particularly preferably. The sulfur-containing compound is a compound that contains a sulfureous component, or a compound that contains a sulfur component capable of being converted to a sulfureous component by subsequent calcining or another treatment. Examples of such sulfur-containing compounds include sulfuric acid, ammonium sulfate, sulfurous acid, ammonium sulfite, thionyl chloride, dimethylsulfuric acid, and the like. The sulfur-containing compound is commonly used as a solution such as an aqueous solution, and the solution is brought into contact with the tin oxide.

Calcining is performed in air, nitrogen, or another gas atmosphere, although performing the process in air is particularly preferred. The calcining temperature varies with the calcining time, gas flow rate, and other calcining conditions, and is commonly 300 to 900° C., and preferably 400 to 800° C. The calcining time varies with the calcining temperature, gas flow rate, and other calcining conditions, and is commonly 0.05 to 20 hours, particularly preferably 0.1 to 10 hours, and still more preferably 0.2 to 5 hours.

Prior to contact with the sulfur-containing compound, the surface of the tin oxide is preferably pretreated with a solution, particularly an aqueous solution, comprising organic acid ions, particularly carboxylic acid ions. An aqueous solution of ammonium acetate or another ammonium carboxylate or carboxylic acid metal salt is preferably used as such an aqueous solution.

Group IV Metal/Group VI Metal-Based Catalyst

Group IV metal/Group VI metal-based Catalyst comprise, as their metal components, one or more Group IV metal components selected from the group comprising titanium, zirconium, and hafnium, and one or more Group VI metal components selected from the group comprising tungsten and molybdenum. Especially, tungsten/zirconia-based catalysts comprising zirconium as the Group IV metal component and tungsten as the Group VI metal component are preferred. Generally, it is known that this type of catalyst has a Hammett acidity function Ho of −14.6. The content of the Group IV metal component in the catalyst is preferably 10 to 72 wt %, and particularly preferably 20 to 60 wt %, in terms of the weight of the Group IV metal element. The content of the Group VI metal component in the catalyst is preferably 2 to 30 wt %, particularly preferably 5 to 25 wt %, and still more preferably 10 to 20 wt %, in terms of the weight of the Group VI metal element. The support is preferably substantially composed of a metal oxide. "Metal oxide" is defined as one comprising a hydrated metal oxide.

In addition to oxides that may comprise hydrated oxides, the support may also comprise other metal components, for example, boron, magnesium, aluminum, silicon, phosphorus, calcium, vanadium, chromium, manganese, iron, cobalt, nickel, copper, zinc, gallium, germanium, yttrium, niobium, tin, lanthanum, cerium, and the like, either singly or in combinations thereof, as well as zeolites and other complex metal oxides. In particular, the catalyst preferably comprises aluminum in an amount of 3 to 30 wt %, and particularly preferably 5 to 25 wt %, in terms of the weight of the aluminum element. Halogens may also be contained as needed in order to enhance the acid catalyst performance. The catalyst does not necessarily have to contain a sulfureous component, but when a sulfureous component is contained, the proportion of the sulfureous component ($SO_4$) in the catalyst, expressed as the weight of the sulfur element, is commonly 0.1 wt % or less.

When the portion of Group IV metal component is made up of zirconia, the zirconia portion preferably substantially comprises tetragonal zirconia. This can be confirmed by powder X-ray analysis or, in more specific terms, by the diffraction peak of tetragonal zirconia at 2θ=30.2° with the CuKα line. It is preferable that crystallization proceed to an extent that can be confirmed by means of a diffraction peak, and that no monoclinic zirconia be contained. Specifically, the ratio S28/S30 is preferably 1.0 or less, and particularly preferably 0.05 or less, where S30 is the area of the diffraction peak of tetragonal zirconia with 2θ=30.2°, and S28 is the area of the diffraction peak of monoclinic zirconia with 2θ=28.20. If an alumina portion is present, the alumina preferably is crystalline, and particularly preferably consists substantially of γ-alumina.

Method of Producing Group IV Metal/Group VI Metal-Based Catalyst

There are no particular limitations on the method of producing the solid acid catalyst, but to give an example, a producing method can be used in which the group VI metal compound(s) is/are added to a powder (hereinafter referred to as the 'precursor powder') of hydrated metal oxide(s) and/or metal hydroxide(s) that constitutes a precursor for the metal oxide(s) of the group IV metal component(s) constituting the support, and then kneading, shaping and calcining are carried out to produce the catalyst. Hereinafter, description will be given for this method, but the order of shaping/calcining the support, mixing in the group VI metal component(s) and so on can be modified.

Precursor Powder of Group IV Metal Oxide

The precursor powder of oxide(s) of group IV metal(s) selected from titanium, zirconium and hafnium becomes the metal oxide(s) constituting the support through calcination after shaping; the precursor powder may be produced in any way, but generally can be obtained by neutralizing or hydrolyzing metal salt(s), organometallic compound(s) or the like, washing and drying. Zirconium hydroxide (including the hydrated oxide) is preferably used as the group IV metal component precursor powder. It is preferable to add a hydrated alumina such as boehmite to the precursor powder. Furthermore, composite metal hydroxide(s) and/or composite metal hydrated oxide(s) can also be used in the precursor powder. The amount added of the group IV metal oxide precursor powder is preferably such that the content of the group IV metal component(s) in the solid acid catalyst ultimately obtained is 10 to 72 wt. %, particularly preferably 20 to 60 wt. %, in terms of the weight of the metallic element(s).

Group VI Metal Compound(s)

Examples of the group VI metal compound(s) are oxides, chlorides, sulfates, nitrates and so on of tungsten or molybdenum, but a heteropolyacid of tungsten or molybdenum is preferably used, and a tungstate or molybdate is most preferably used. The group VI metal compound(s) may be used as is, or as a solution such as an aqueous solution. The group VI metal compound(s) may be in a solid or liquid state, and there are also no particular limitations on the concentration of a solution, with it being possible to prepare the solution while considering the amount of solution required for the kneading and so on. The amount added of the group VI metal compound(s) is preferably made to be such that the content of the group VI metal component(s) in the solid acid catalyst ultimately obtained is 2 to 30 wt. %, preferably 5 to 25 wt. %, particularly preferably 10 to 20 wt. %, in terms of the weight of the group VI metallic element(s).

Kneading

There are no particular limitations on the kneading method, with it being possible to use a kneader generally used in catalyst preparation. In general, it is preferable to use a method in which the raw materials are put into the kneader, a solvent such as water is added, and kneading is carried out using agitating blades, but there are no particular limitations on the order of putting in the raw materials and additives. During the kneading, water is generally added as the above-mentioned solvent, but an organic solvent such as ethanol, isopropanol, acetone, methyl ethyl ketone, or methyl isobutyl ketone may be added. The temperature during the kneading and the kneading time vary according to the precursor powder of hydrated metal oxide(s) and/or metal hydroxide(s), which constitutes a raw material, and so on, but there are no particular limitations so long as these conditions are such that a preferable pore structure can be obtained. Similarly, acids such as nitric acid, bases such as ammonia, organic compounds, metal salts, ceramic fibers, surfactants, zeolites, clays, and so on may be added when carrying out the kneading, so long as this is within a range such that the properties of the catalyst of the present invention are maintained.

Shaping

There are no particular limitations on the method of shaping after kneading, with it being possible to use a shaping method generally used in catalyst preparation. In particular, it is preferable to use extrusion shaping using a screw extruder or the like, since shaping into a desired shape such as pellets or a honeycomb can be carried out efficiently. There are no particular limitations on the size of the shaped article but, in general, the shaping is carried out to a size such that the length of the cross section of the shaped article is 0.5 to 20 mm. For example, in the case of cylindrical pellets, in general, ones having a diameter of 0.5 to 10 mm and a length of approximately 0.5 to 15 mm can be obtained easily.

Calcining after Shaping

After the shaping, calcining is carried out in an atmosphere of a gas such as air or nitrogen, although it is particularly preferable to carry out the calcining in air. The calcining temperature varies according to the other calcining conditions such as the calcining time and the gas circulation rate, but is generally 400 to 900° C., preferably 500 to 800° C. The calcining time varies according to the other calcining conditions such as the calcining temperature and the gas circulation rate, but is generally preferably 0.05 to 20 hours, particularly preferably 0.1 to 10 hours, more preferably 0.2 to 5 hours.

Transesterification Reaction

The reaction temperature is such that the starting material ester is in a liquid state, and the alcohol is in a vapor state; specifically, the temperature is preferably 100° C. or greater, and particularly preferably 150 to 350° C. The reaction pressure is not particularly limited and may be about 0.1 to 100 atm. Although the reaction will also progress adequately at 0.5 to 2 atm, which is roughly equal to atmospheric pressure, it is preferred to conduct the reaction under 2 to 100 atm, especially under 10 to 50 atm in which tungsten/zirconia-based catalysts are preferably employed. The reaction may also be conducted in the so-called supercritical state. Nor is the reaction time limited, and the product can be obtained in an adequate amount in about 0.1 to 1 hour in a batch reaction, and at a WHSV (weight hourly space velocity) of about 0.5 to 5 (/hour) in a flow reaction. The reaction may be a batch type, flow type, or the like.

EXAMPLES

A more detailed description will be given below with the aid of examples.

Preparation of Sulfated Zirconia-Based Catalyst SZA

A powder that had a mean grain size of 1.5 μm and was obtained by drying commercially available dried zirconia hydroxide was used as the hydrated zirconia powder. Also, a commercially available pseudoboehmite powder with a mean grain size of 10 μm was used as the hydrated alumina powder. 1860 g of the hydrated zirconia powder and 1120 g of the hydrated alumina powder were blended, 575 g of ammonium sulfate was further added, and the ingredients were kneaded for 45 minutes with a kneader fitted with stirring blades while water was added. The resulting blend was extruded from an extruder having a circular opening with a diameter of 1.6 mm, cylindrical pellets were molded, and the pellets were dried at 110° C., yielding dried pellets. Some of the dried pellets were subsequently calcined at 675° C. for 1.5 hours, yielding a sulfated zirconia-based catalyst (referred to hereinbelow as "SZA"). The zirconia portion of the catalyst thus obtained consisted essentially of tetragonal zirconia.

SZA was used after cylindrical shapes with a mean diameter of 1.4 mm and a mean length of 4 mm obtained by calcining had been graded to a size of 16 to 24 mesh. SZA had a specific surface area of 158 m$^2$/g, and the pore volume of pores with diameters of 0.002 to 10 μm was 0.31 cm$^3$/g. The central pore diameter of SZA whose pore diameters were in the range 0.002 to 0.05 μm was 5.5 nm. The argon adsorption heat was 24.3 kJ/mol.

Preparation of Sulfated Tin Oxide-Based Catalyst MO-817

100 g of commercially available metastannic acid (SnO$_2$, manufactured by Yamanaka Industry) was dispersed in a 4-wt % aqueous solution of ammonium acetate, and the solution was filtered and dried for 24 hours in air at 100° C., yielding precursor 1.4 g of the precursor 1 thus obtained was brought into contact with 60 mL of 6N sulfuric acid for 1 hour, filtered, dried for 2 hours in air at 100° C., and calcined for another 3 hours in air at 500° C., yielding a sulfated tin oxide-based catalyst (referred to hereinbelow as "MO-817"). The tin oxide portion of the catalyst thus obtained consisted essentially of tetragonal tin oxide.

MO-817 was in the form of a powder and had a specific surface area of 152 m$^2$/g, and the pore volume of pores with diameters of 0.002 to 10 μm was 0.1 cm$^3$/g. The central pore diameter of MO-817 whose pore diameters were in the range 0.002 to 0.05 μm was 2.8 nm. The argon adsorption heat was 31.0 kJ/mol.

Preparation of Tungsten/Zirconia-Based Catalyst MO-850

A powder that had a mean grain size of 1.5 μm and was obtained by drying commercially available dried zirconia hydroxide was used as the hydrated zirconia powder. Also, a commercially available pseudoboehmite powder with a mean grain size of 10 μm was used as the hydrated alumina powder. 1544 g of the hydrated zirconia powder and 912 g of the hydrated alumina powder were blended, 808 g of ammonium metatungstate was further added, and the ingredients were kneaded for 25 minutes with a kneader fitted with stirring blades while 1200 g of water was added. The resulting blend was extruded from an extruder having a circular opening with a diameter of 1.6 mm, cylindrical pellets were shaped, and the pellets were dried at 110° C., yielding dried pellets. Some of the dried pellets were subsequently calcined at 800° C. for 1 hour, yielding a tungsten/zirconia-based catalyst (referred to hereinbelow as "MO-850"). The zirconia portion of the catalyst thus obtained consisted essentially of tetragonal zirconia.

MO-850 had a cylindrical shape with an average diameter of 1.4 mm and an average length of 4 mm, and had a mean crushing strength of 1.9 kg. The specific surface area was 101 m$^2$/g, the pore volume of pores with diameters of 0.002 to 10 μm was 0.32 cm$^3$/g, and the central pore diameter in the pore diameter range 0.002 to 0.05 μm was 105 Å. The proportion of zirconia in MO-850, in terms of the weight of the zirconium element, was 38.0 wt %; the proportion of alumina, in terms of the weight of the aluminum element, was 13.0 wt %; the proportion of the tungstic acid component, in terms of the weight of the tungsten element, was 12.5 wt %; and the proportion of the sulfur component was 0.01 wt % or less. The argon adsorption heat was 17.6 kJ/mol.

Transesterification Reaction

These catalysts (4 cm$^3$) were charged into a fixed-bed flow reactor with a length in the vertical direction of 50 cm and an inside diameter of 1 cm and then soybean oil (manufactured by Kanto Kagaku) as a starting material ester and methanol as alcohol were introduced from the top under atmospheric pressure. The transesterification reaction was carried out under the conditions shown in Tables 1 and 2, and the conversion rate of the soybean oil at the bottom outlet was measured by gas chromatography after 4 hours and 20 hours from the start of the reaction. The molar ratio of soybean oil and methanol was set to 1:40. The experimental results are shown in Tables 1 and 2. A catalyst-free product obtained by charging the same volume of α-alumina powder instead of the catalyst was measured for comparison purposes.

TABLE 1

| | Experimental Example | | | | | | |
|---|---|---|---|---|---|---|---|
| | 1 | 2 | 3 | 4 | 5 | 6 | 7 |
| Catalyst | SZA | SZA | SZA | SZA | MO-817 | MO-817 | MO-817 |
| Reaction temperature (° C.) | 200 | 200 | 250 | 300 | 200 | 250 | 300 |
| WHSV (/hour) Flow rate of starting material (g/hour) | 1.5 | 1.85 | 1.85 | 1.85 | 1.85 | 1.85 | 1.85 |
| Soybean oil | 3.3 | 3.0 | 3.0 | 3.0 | 3.0 | 3.0 | 3.0 |
| Methanol | 2.7 | 4.4 | 4.4 | 4.4 | 4.4 | 4.4 | 4.4 |
| Conversion rate of soybean oil (%) | | | | | | | |
| After 4 hours | 45 | 37 | — | 93 | — | — | 69 |
| After 20 hours | 41 | 27 | 56 | 78 | 10 | 18 | 67 |

TABLE 2

| | Experimental Example | | | |
|---|---|---|---|---|
| | 8 | 9 | 10 | 11 |
| Catalyst | MO-850 | MO-850 | MO-850 | None |
| Reaction temperature (° C.) | 200 | 250 | 300 | 200 |
| WHSV (/hour) Flow rate of starting material (g/hour) | 1.85 | 1.85 | 1.85 | — |
| Soybean oil | 3.0 | 3.0 | 3.0 | 3.0 |
| Methanol | 4.4 | 4.4 | 4.4 | 4.4 |
| Conversion rate of soybean oil (%) | | | | |
| After 4 hours | 48 | 86 | — | 0 |
| After 20 hours | 47 | 89 | 93 | 0 |

It was learned that although soybean oil was transesterified when a very strong acid catalyst was used, SZA was susceptible to deterioration during the reaction, whereas MO-817 showed a low conversion rate, especially at the reaction temperature of 250° C. or less. The highest conversion rate was obtained when MO-850 was used and this catalyst was not subject to degradation during the reaction.

Further, a transesterification reaction was similarly carried out under the reaction conditions shown in Table 3 in which the reaction pressure was changed to 3.0 MPa.

TABLE 3

|  | Experimental Example | | |
|---|---|---|---|
|  | 12 | 13 | 14 |
| Catalyst | SZA | MO-817 | MO-850 |
| Reaction temperature (° C.) | 250 | 250 | 250 |
| Reaction pressure (MPa) | 3.0 | 3.0 | 3.0 |
| WHSV (/hour) | 1.85 | 1.85 | 1.85 |
| Flow rate of starting material (g/hour) | | | |
| Soybean oil | 3.0 | 3.0 | 3.3 |
| Methanol | 4.4 | 4.4 | 4.4 |
| Conversion rate of soybean oil (%) | | | |
| After 20 hours | 88.0 | 61.0 | 91.0 |

It is clear that the above catalysts all increased the conversion rate under the pressurized condition. Especially, it is noted that the use of MO-850 provided a further improved conversion rate in the reaction under such a pressurized condition, although it provided a fully enhanced conversion rate in the reaction under atmospheric pressure.

INDUSTRIAL APPLICABILITY

According to the present invention, a transesterification reaction can proceed in a short time under a pressure that is approximately equal to normal pressure, and the product and catalyst can be easily separated. It is therefore possible to produce the desired ester with a high efficiency.

The invention claimed is:

1. A method for producing an ester in which the ester is produced by a transesterification reaction comprising the step of bringing a starting material ester and an alcohol into contact with a solid acid catalyst that displays the characteristics of a very strong acid in terms of the absolute value of argon adsorption heat ranging from 15 to 22 kJ/mol, the solid acid catalyst comprising a Group IV metal component in a content of 10 to 72 wt %, in terms of the weight of the Group IV metal element, and a Group VI metal component in a content of 2 to 30 wt %, in terms of the weight of the Group VI metal element.

2. The method for producing an ester according to claim 1, wherein the starting material ester is in a liquid phase and the alcohol is in a vapor phase.

3. The method for producing an ester according to claim 1, wherein the starting material ester is an oil or a fat, and the alcohol is methanol or ethanol.

4. The method for producing an ester according to claim 1, wherein the Group IV metal component is zirconium and the Group VI metal component is at least one member selected from the group consisting of tungsten and molybdenum.

5. The method for producing an ester according to claim 1, wherein the catalyst comprises aluminum in an amount of 3 to 30 wt %, in terms of the weight of the aluminum element.

6. The method for producing an ester according to claim 1, wherein the catalyst does not contain a sulfureous component.

* * * * *